United States Patent
Zhang et al.

(10) Patent No.: US 7,226,010 B2
(45) Date of Patent: Jun. 5, 2007

(54) METHOD AND APPARATUS FOR SOLID FUEL PULVERIZING OPERATION AND MAINTENANCE OPTIMIZATION

(75) Inventors: George Zhang, Windsor, CT (US); Paul C. Thulen, Granby, CT (US); Zhongxue Gan, Windsor, CT (US)

(73) Assignee: ABB Inc., Norwalk, CT (US)

( * ) Notice: Subject to any disclaimer, the term of this patent is extended or adjusted under 35 U.S.C. 154(b) by 16 days.

(21) Appl. No.: 10/788,848

(22) Filed: Feb. 27, 2004

(65) Prior Publication Data

US 2005/0263630 A1    Dec. 1, 2005

(51) Int. Cl.
B02C 15/04    (2006.01)
B02C 15/00    (2006.01)

(52) U.S. Cl. .................. 241/121; 241/117; 241/118; 241/119; 241/120

(58) Field of Classification Search ............ 241/117, 241/118, 119, 120, 121
See application file for complete search history.

(56) References Cited

U.S. PATENT DOCUMENTS

| | | | |
|---|---|---|---|
| 4,190,005 A | 2/1980 | Cookson et al. | |
| 4,310,298 A | 1/1982 | Abelitis | |
| 4,432,500 A | 2/1984 | Brundiek et al. | |
| 4,705,223 A | 11/1987 | Dibowski et al. | |
| 4,717,084 A * | 1/1988 | Vendelin et al. | 241/207 |
| 4,798,342 A * | 1/1989 | Williams | 241/18 |
| 4,885,707 A | 12/1989 | Nichol et al. | |
| 5,039,021 A | 8/1991 | Eisinger | |
| 5,230,474 A | 7/1993 | Yamaguchi et al. | |
| 5,244,157 A * | 9/1993 | Brundiek | 241/36 |
| 5,277,134 A | 1/1994 | Schlessing et al. | |
| 5,593,131 A | 1/1997 | Briggs, Jr. et al. | |
| 5,996,916 A * | 12/1999 | Musil | 241/215 |
| 6,004,097 A | 12/1999 | Wark et al. | |
| 6,189,819 B1 | 2/2001 | Racine | |
| 6,347,757 B1 | 2/2002 | Takahashi et al. | |

FOREIGN PATENT DOCUMENTS

JP     2001 017880 A     1/2001
WO  PCT/US2005/005903    2/2005

OTHER PUBLICATIONS

Revolutionary Science, 2001, Spintelligent Labs, SP002332902, Predictive Maintenance FAQ, Retrieved from the Internet.

* cited by examiner

Primary Examiner—Lowell A. Larson
Assistant Examiner—Jason Y. Pahng
(74) Attorney, Agent, or Firm—Michael M. Rickin

(57) ABSTRACT

A system for use with a roll bowl type mill for the pulverizing of solid fuels such as coal. The system includes hardware in the form of sensors and other components and software to among other things monitor the operating condition of the mill's moving parts and predict their failure. The system can determine the diameter of the mill's rollers, or the reduction and/or depth of cup wear of each of the rollers, the thickness of the solid fuel in the mill, can by analysis determine the wear of each of the one or more roller bearings in the mill and predict their failure and can estimate the mill availability.

11 Claims, 9 Drawing Sheets

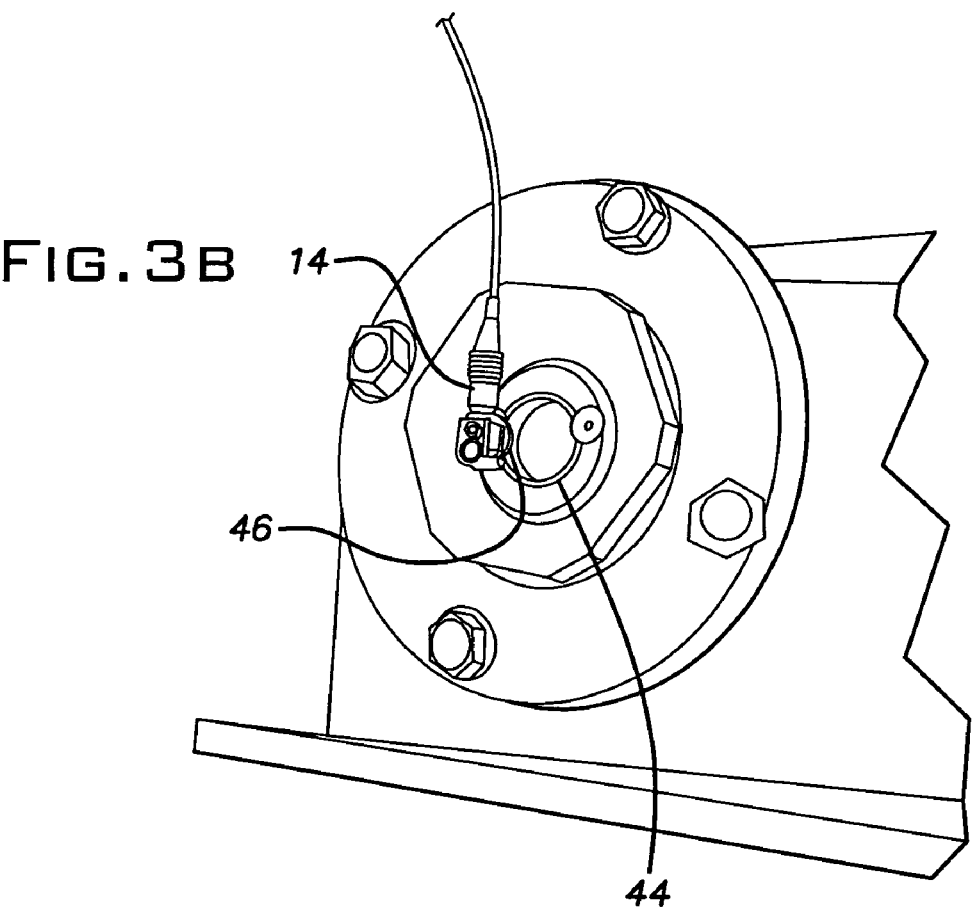
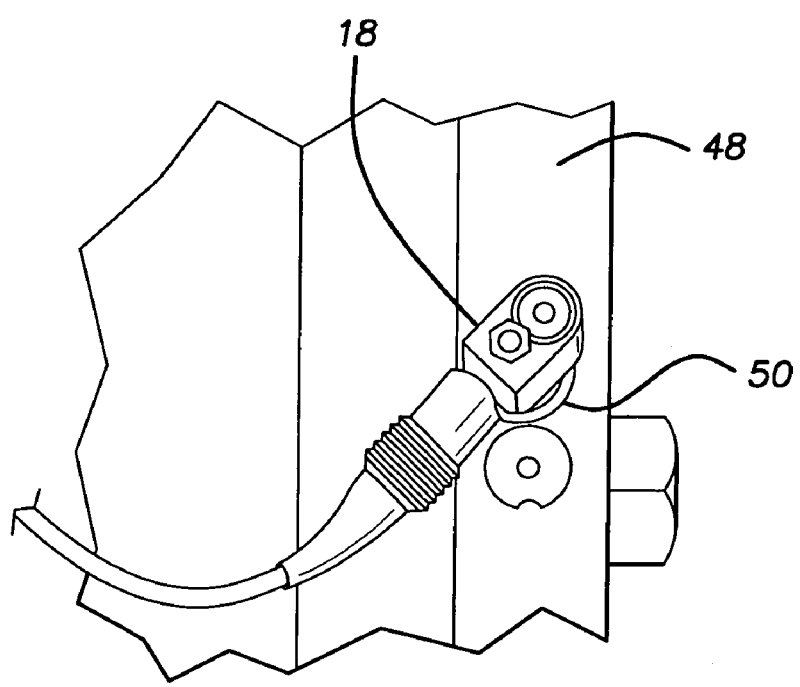

METHOD AND APPARATUS FOR SOLID FUEL PULVERIZING OPERATION AND MAINTENANCE OPTIMIZATION

FIELD OF THE INVENTION

This invention relates to the pulverizing of solid fuels such as coal in power generation plants and more particularly to the monitoring of and scheduling of maintenance for the pulverizer.

DESCRIPTION OF THE PRIOR ART

One of the most significant engineering achievements of the twentieth century is the commercial perfection of the coal pulverizer and methods for firing coal in pulverized form in a power generation plant. The function of a pulverizer in a coal combustion system is to reduce the size of the coal particles to fine powder. The reason for this is to increase the combustibility of the coal and the efficiency of the system.

The development of the coal pulverizer is one of the cornerstones making possible the extremely large, modern, steam-generating unit with its high thermal efficiency, reliability and safety. Worldwide, almost all kinds of coal is being burned with complete success in pulverized form. Similarly, many other type of low-grade, waste, and byproduct solid fuels may also be fired economically and efficiently in this manner.

The four main types of pulverizers are:
Ball Tube
Roll-Bowl or Ball Race
Impact or Hammer Pulverizer Mill
Attrition Type Each of the above types of pulverizers employs a different method of reducing the size of the coal particles. The variation in the design of these machines accounts for different characteristics in operation and maintenance. Across the design spectrum there can be found different aspects of operation that are more suited to different applications. Each one of the above four main pulverizer types are briefly described below.

Ball Tube Mill

The Ball Tube type pulverizers are made up of a large cylinder loaded to slightly less then half way with forged steel or cast alloy balls ranging from one to four inches in diameter. The coal is brought into the mill through piping, which directs the coal into screw loaders located at the sides of the cylinder. The coal is gravity fed into the system through the feeder, which governs the amount of coal delivered to the machine upon loading. The cylinder is lined with a wear resistant cast material that will not need to be replaced for years of use.

The Ball Tube type mill rotates the cylinder with the balls and coal at a speed of about 18 to 35 rpm. This rotation causes the coal to be reduced in size through crushing under the alloy balls as well as wear from friction against the balls, liners and other coal particles, resulting from the rotational motion of the cylinder. A classifier is often used with this system in order to control the size of the coal particles that reach the burner. This type of pulverizer is considered to be a low speed machine.

Roll-Bowl or Ball Race Mill

Roll-Bowl or Ball Race is the name given to the pulverizer, which uses a Ring-Roll or Ball-Race combination in order to achieve the particle reduction of coal fuel. When the Ball-Race combination is used, the Balls are confined between two races. The races consist of two channels that are shaped such that the balls roll freely inside them. The races are held together by means of springs or some type of pneumatic or hydraulic rams. It is this applied pressure that gives the grinding force needed for the coal particles to be reduced. The lower race is generally driven in this machine but some designs use both races as the driving mechanism. When the Roll-Bowl combination is used, it is possible to drive the Bowl or the Roll.

In either case the grinding force is obtained through the centrifugal force of the rollers. The pulverizer which uses the stationary rolls and the rotating ring are the most widely used type of pulverizer today. This type of machine also has a classifier that governs the particle sizes of the coal before they enter the burners. The coal is loaded through the center of the system by means of a pipe that travels through the machine. The coal is gravity fed and the amount of coal entering the system at one time is controlled by a feeder system. This system is a medium speed system.

Impact or Hammer Pulverizer Mill

An Impact or Hammer pulverizer mill uses the impact of the hammers on the coal particles as well as attrition with the smaller particles to obtain the particle size reduction. The machine is made of up a series of hammers that can be both hinged and fixed in positions. The coal is loaded into the system through one side and uses gravity to pull the coal into the area of the mill that causes the size reduction. These hammers revolve in an enclosed chamber lined with wear resistant materials. This design is considered to be a high speed Pulverizer. The speed causes wear problems, which also cause particle uniformity problems during the life of the system. The system may also have a classifier allowing the coal particle size to be monitored into the burner.

Attrition Type Mill

The Attrition mill, which is a high speed system, is not used for direct pulverization of coal due to the high wear of the machine parts. The main use of this type of pulverizer is the direct firing of pulverized coal. A rotating disc inside of an enclosed cylinder achieves the particle reduction. The disc has rows of pegs and lugs. The cylinder is lined with wear resistant materials and the pegs and lugs on the disc are also made from wear resistant materials to increase the life of the system. The high-speed of this mill is the main cause for the high wear of the machine and thus the short operating life of this system.

The Pulverizer's Importance

As is described above the purpose of the pulverizer is to reduce the size of the coal particles. The question is why is that important to the power generation process? The answer lays in the efficiency and emission problems faced by coal fired power plants today. These are extremely important factors in any process involving combustion due to the current state of the environment and cost reduction trends. The U.S. and other countries are putting a lot of effort into the improvement of the combustion of coal for power generation. This makes the pulverizer a very important asset to the plants as well as an asset, which cannot be replaced.

The pulverizer is also very important to the performance of the plant for which it serves. This is the first process in the chain of power generation and the most time consuming. The pulverizer is responsible for drying and crushing the correct amount of coal according to how much power the plant has to generate. If the pulverized coal is not there to burn, the plant is unable to produce the power and will lose time, money and credibility in the grid it is supplying. Further poor operation or even failure of the coal pulverizer leads at best to plant de-rating or at worst unit shutdown. These things make the pulverizer a very essential part of the coal fired power production system, and justify improvements to both the pulverizer and its operation.

As is described above, the coal pulverizer is essential to the use of coal in power generation. The pulverizer, which is located at the beginning of the process in the coal-fired power plant, crushes the coal into a fine power in order to be burned efficiently in the furnace. As is described below there are problems associated with the use of pulverizers in power plants and the occurrence of one or more of these problems can cause the pulverizer to be a "bottle neck" for the whole power generation process The major problems with pulverizers are:

Dynamic unbalance—vibration
Wear and failure of moving parts
Lack of fineness, flow rate measurement and control
Lack of failure detection and maintenance scheduling tools
Slow response to the variation of the feed rate
Outlet distribution imbalance
Overloading related problems
Pulverizer fire.

Vibration and wear which is the cause of major part failure in the pulverizer and the lack of failure detection and maintenance scheduling tools have been identified as critical problems. Currently, there is no system or apparatus that can take care of these problems. Operation conditions and failures are now mainly determined by operator experience. The severe conditions around the coal mill prevents continuous monitoring of the mill's operating condition and prompt notification of the occurrence of a problem. Power generation capacity de-rating, damaging of the mill main driving shaft and even shutting down the plant sometime occur due to lack of checking up and on-time maintenance. Further, since there is today not any instrumentation to tell the operating condition for moving parts such as roller and roll bearings located inside of the mill, the power generation plant may perform unnecessary maintenance which increases the cost of power generation.

The present invention which is a hardware/software system that monitors coal mill operating condition, detects and predicts mill failure, schedules maintenance activities and estimates coal fineness of the pulverized coal in order to optimize the coal pulverizing process for the power generation plant solves the critical problems described above.

SUMMARY OF THE INVENTION

In combination:
a roll-bowl type mill for pulverizing solid fuels for use in firing a steam generator, the pulverizing mill comprising:
a) a bowl having a predetermined diameter;
b) one or more rollers each connected to an assembly through an associated roller bearing, the assembly for holding each of the one or more rollers and for applying a preload on each of the one or more rollers, each of the one or more rollers located a predetermined distance above the bowl; and
c) one or more linear transducers mounted on the assembly to measure the displacement of the movement of the assembly when the mill is operating;
a data acquisition system having as an input the assembly movement displacement measured by the one or more linear transducers comprising:
a computing device for data collection and frequency power spectrum analysis of the assembly shaft displacement to determine:

a) the diameter, D, of each of the one or more rollers by using the formula:

$$D = F_b/F_r D_b$$

where, $F_b$ is the bowl frequency and $F_r$ is the roller frequency determined by power spectrum analysis respectively, and $D_b$ is the bowl predetermined diameter.

In combination:
a roll-bowl type mill for pulverizing solid fuels for use in firing a steam generator, the pulverizing mill comprising:
a) a bowl having a predetermined diameter;
b) one or more rollers each connected to an assembly through an associated roller bearing, the assembly for holding each of the one or more rollers and for applying a preload on each of the one or more rollers, the one or more rollers located a predetermined distance above the bowl; and
c) one or more linear transducers mounted on the assembly to measure the displacement of the movement of the assembly when the mill is operating;
a data acquisition system having as an input the assembly movement displacement measured by the one or more linear transducers comprising:
a computing device for data collection and frequency power spectrum analysis of the assembly shaft displacement to determine the reduction and/or depth of wear cup, H, of each of the one or more rollers by using the formula:

$$D_1 = 2R_1 = \frac{F_b}{F_{r1}} D_b$$

$$D_2 = 2R_2 = \frac{F_b}{F_{r2}} D_b$$

$$H = R_1 - R_2 = \frac{|F_{r2} - F_{r1}| F_b D_b}{2 F_{r1} F_{r2}}$$

where, $F_{r1}$ is the dominant roller frequency peak from power spectrum analysis $F_{r2}$ is the secondary roller frequency peak from power spectrum analysis.

In combination:
a roll-bowl type mill for pulverizing solid fuels for use in firing a steam generator, the pulverizing mill comprising:
a) a bowl having a predetermined diameter;
b) one or more rollers each connected to an assembly through an associated roller bearing, the assembly for holding each of the one or more rollers and for applying a preload on each of the one or more rollers, the one or more rollers located a predetermined distance above the bowl; and
c) one or more linear transducers mounted on the assembly to measure the displacement of the movement of the assembly when the mill is operating;
a data acquisition system having as an input the assembly movement displacement measured by the one or more linear transducers comprising:
a computing device for data collection and frequency power spectrum analysis of the assembly shaft displacement to determine the relative thickness of the solid fuel in the mill by using the formula:

$$L_1 = \beta \frac{|L| - |L_0|}{|L_0|},$$

where L is the value of the displacement of the journal spring shaft measured by the one or more linear transducers, $L_0$ is the calibrated value from the one or more transducers, and $\beta$ is a coefficient.

A system comprising:

a mill for pulverizing solid fuels for use in firing a steam generator, the mill comprising a predetermined number of components used in pulverizing the solid fuel; and a processing device for determining an indicator P, where $0 \leq P \leq 1$, for presenting the availability of the mill to perform the solid fuel pulverizing by using the formula:

$$P = \sum_{1}^{n} w_i p_i$$

where $w_i$ is the weight factor, $\Sigma w_i = 1$; and $p_i$ is the availability of each individual component of the predetermined number of components and $0 \leq p_i \leq 1$.

An apparatus for use with a mill for pulverizing solid fuels for use in firing a steam generator, the mill comprising a predetermined number of components used in pulverizing the solid fuel, the apparatus comprising:

a computing device for determining an indicator P, where $0 \leq P \leq 1$, for presenting the availability of the mill to perform the solid fuel pulverizing by using the formula:

$$P = \sum_{1}^{n} w_i p_i$$

where $w_i$ is the weight factor, $\Sigma w_i = 1$; and $p_i$ is the availability of each individual component of predetermined number of components and $0 \leq p_i \leq 1$.

A computer readable medium having instructions for causing a computer to execute a method comprising:

determining an indicator P, where $0 \leq P \leq 1$, for presenting the availability of a mill for pulverizing solid fuels for use in firing a steam generator, the mill comprising a predetermined number of components used in pulverizing the solid fuel, to perform the solid fuel pulverizing by using the formula:

$$P = \sum_{1}^{n} w_i p_i$$

where $w_i$ is the weight factor, $\Sigma w_i = 1$; and $p_i$ is the availability of each individual component of predetermined number of components and $0 \leq p_i \leq 1$.

A method for determining the availability of a mill for pulverizing solid fuels for use in a firing a steam generator, the mill having a predetermined number of components used in pulverizing the solid fuel comprising:

calculating a mill availability indicator, P, where $0 \leq P \leq 1$, in accordance with the following equation:

$$P = \sum_{1}^{n} w_i p_i$$

where $w_i$ is the weight factor, $\Sigma w_i = 1$; and $p_i$ is the availability of each individual component of the mill and $0 \leq p_i \leq 1$.

In combination:

a roll-bowl type mill for pulverizing solid fuels for use in firing a steam generator, the pulverizing mill comprising:

a) a bowl having a predetermined diameter;

b) a journal assembly;

c) one or more rollers each connected to the journal assembly through an associated roller bearing, each of the one or more rollers located a predetermined distance above the bowl;

d) a journal spring shaft accessible from outside of the mill and connected onto the journal assembly, the movement of the journal assembly measurable through the journal spring shaft;

e) a wall; and f) a trunion shaft, one or more vibration sensors mounted on the end of the trunion shaft to measure the vibration of the trunion shaft when the mill is operating, the trunion shaft connecting the journal assembly onto the mill wall; and a data acquisition system having as an input the trunion shaft vibration measured by the one or more vibration sensors, the having comprising:

a computing device for predicting failure of each of the one or more the roller bearing from the trunion shaft vibration measured by the one or more vibration sensors by first transferring the measured shaft vibration to the location of each of the one or more roller bearings by a predetermined transfer function and then determining wear for each of the one or more roller bearings by analyzing using vibration pattern signature and/or order analysis methods the transferred signal from each of the one or more vibration sensors.

DESCRIPTION OF THE DRAWING

FIGS. 3a to 3c are photographs showing the mounting methods for the sensors used in the mill operation sensing system which is part of the present invention and their location on the Roll-Bowl mill.

DESCRIPTION OF THE PREFERRED EMBODIMENT(S)

The present invention also known as the "mill advisor" is a hardware/software system that includes a sensing system, a data acquisition system, a data processing module, an expert system rules and an error recording and reporting system. The mill operation sensing system includes a displacement sensor, a vibration sensor, and pressure and temperature sensors as well as other sensors.

The data acquisition system may be PC-based as in the embodiment described herein or a module embedded in a power plant control system such as a distributed control system (DCS). The data processing software module uses a vibration signal processing algorithm to monitor the operating condition of the moving parts and predict the failure.

An expert system extracts mill operation and maintenance engineer's knowledge, sets up the rules and generates operation advice and maintenance schedules. Any commercially available expert system software can be used as the expert system in the system of the present invention. The error recording and reporting system is a software module that records the processed history data and sends out a report regularly or a warning when urgent problems occur.

This invention is described herein in connection with the Roll-Bowl type pulverizer which is the most widely used type of pulverizer in the power generation industry. The invention can be used for other types of coal mills as well although some specific functions may need to be modified to fit that particular mill type.

Figure 1:
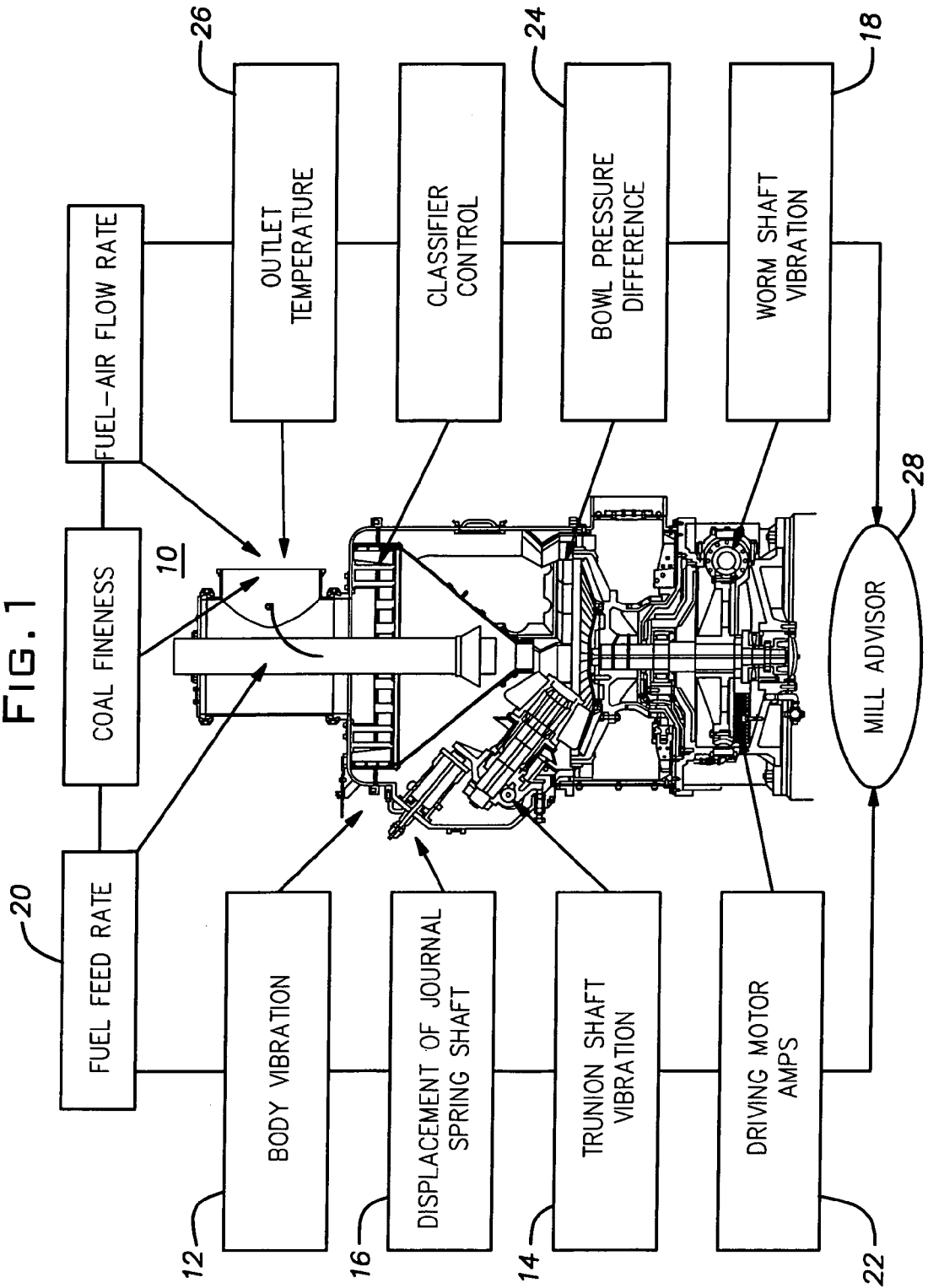
FIG. 1 illustrates the Roll-Bowl coal pulverizer mill including the mill advisor system of the present invention.

FIG. 1 shows symbolically the mill advisor system of the present invention in connection with a Roll-Bowl coal pulverizer mill 10 of the RS type mill sold by the former Combustion Engineering (CE). FIG. 1 also shows the parameters sensed in the mill 10 and the location of the sensors 12–26 on the mill. The sensors 12–26 and their functions are:

Body vibration sensor 12—this sensor is an accelerometer, to monitor overall mill vibration. Analyzing and comparing the signal from this sensor with a benchmark for a particular mill will give the overall health condition and failure prediction for that mill.

Trunion shaft vibration sensors 14—these sensors are accelerometers, to monitor the vibration of the trunion shaft. Analyzing the signal from these sensors will tell the degree of wear of the roller bearing and predict the failure of the bearings. There is one sensor for each of three trunion shafts in pulverizer 10.

Journal spring shaft displacement sensors 16—these sensors are LVDTs, to measure the displacement of the roller journal movement. Analyzing the signal from these sensors can give information on the pulverizing process including the coal depth in the mill 10.

Worm shaft vibration sensor 18—this sensor is an accelerometer, to monitor the worm shaft that is connected to the driving motor shaft. Main gear box unbalance and failure of the main shaft can be obtained from this sensor signal.

Fuel feed rate sensor 20—this sensor measures the coal feed rate.

Motor AMP meter 22—this sensor measures the driving motor power input.

Pressure meter 24—this sensor measures the pressure at different locations inside of the mill 10.

Temperature meters 26—these sensors measure the temperature at different locations in the mill 10.

The mill advisor system of the present invention indicated symbolically by 28 in FIG. 1 collects the information from all of the sensors 12–26 and other operating parameters of the mill 10, analyzes them, and gives advice to the operator, maintenance personnel and management in an on-line manner.

In addition to the sensing system described above, one embodiment for system 28 that was built and tested included the data acquisition system, data processing module, expert system rules for the expert system software used in the present invention and error recording and reporting system described below.

Figure 2:
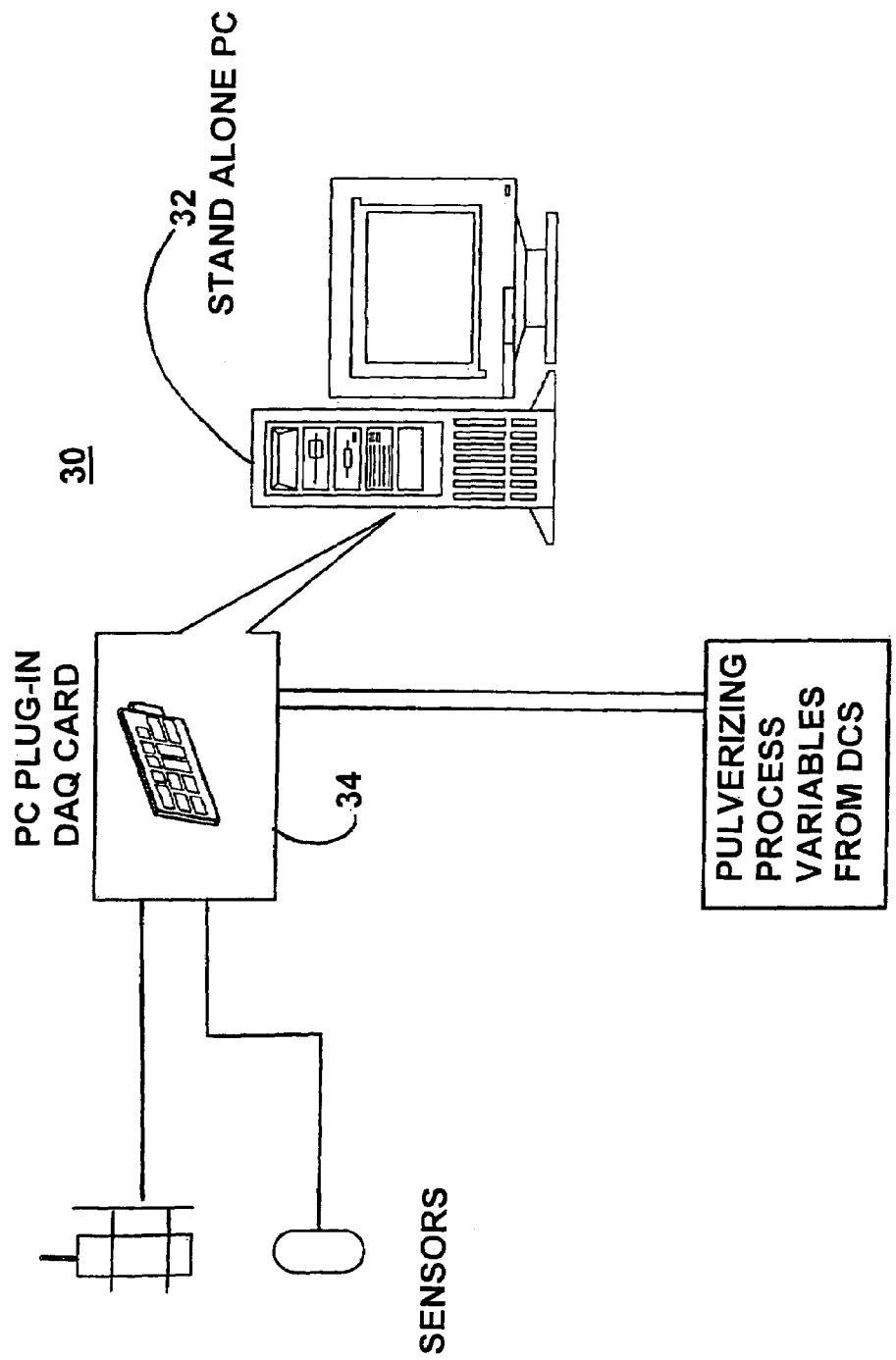
FIG. 2 shows one embodiment for the data acquisition system that is part of the mill advisor system of the present invention.

The data acquisition system 30 for this one embodiment is as is shown in FIG. 2 PC-based. System 30 includes a stand alone PC 32 that has a plug-in data acquisition (DAQ) card 34. The DAQ card 34, which as of the filing date of the U.S. patent application was available from National Instruments, 11500 N Mopac Expwy, Austin, Tex. 78759-3504, acquires the analog signals from the displacement sensor such as LVDT 16, vibration sensors such as accelerometers 12, 14 and 18 as well as process related sensor data such as feed rate from sensor 20 and bowl pressure difference from sensor 22 and the output of sensors 22 and 24.

Figure 3A:
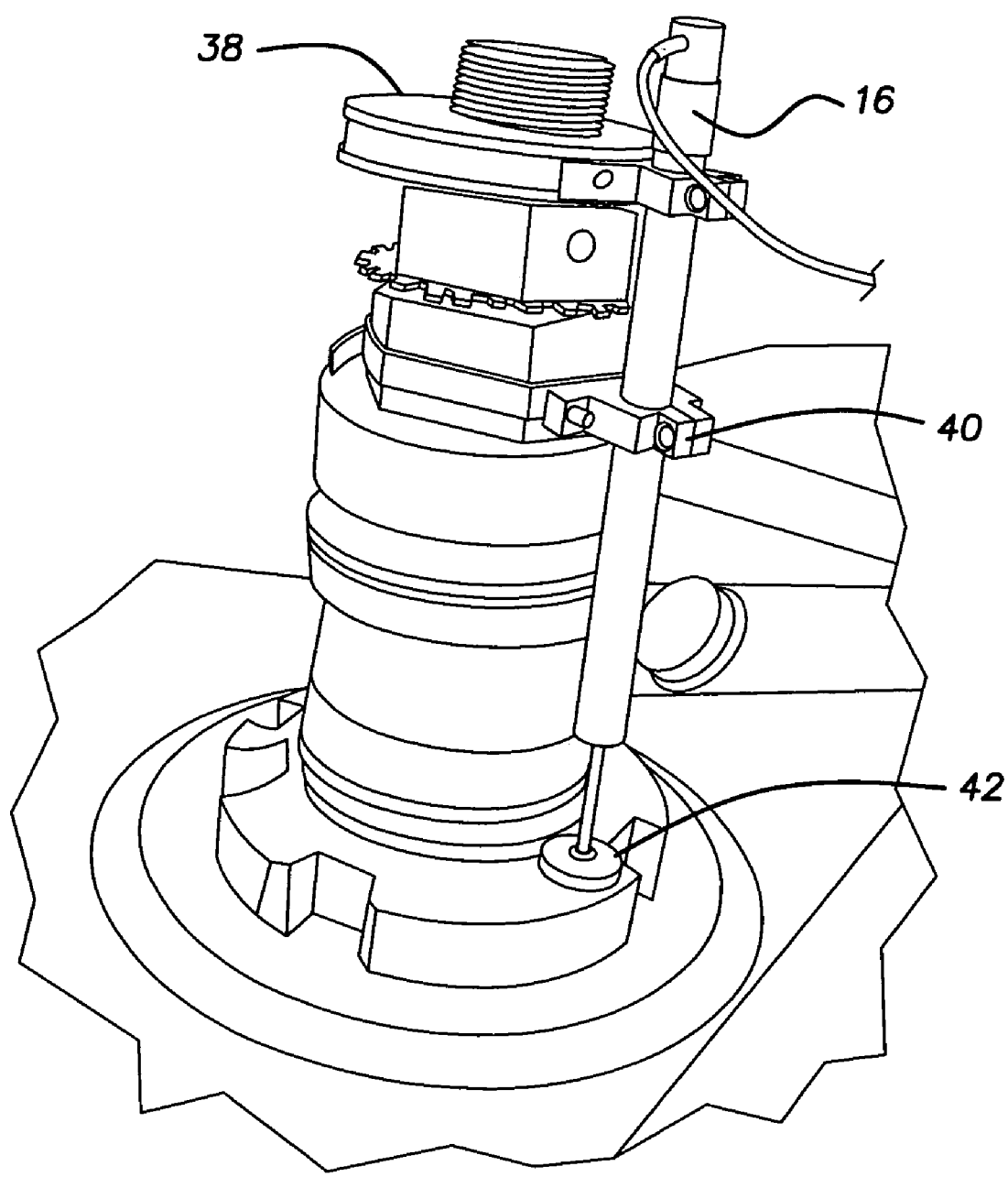

FIGS. 3a–c are photographs showing the mounting methods for the sensors and their locations on the mill 10. The displacement sensor which is a LVDT 16 on the journal spring shaft 38 is placed as is shown in FIG. 3a between the moving journal shaft assembly and the non-moving mill body. A special fixture 40 is used. The fixture is attached on the moving journal shaft assembly and holds the LVDT cylinder. The LVDT probe is screwed on a magnetic pad 42, which is attached on the mill body through magnetic force. The vibration sensor 14 on the Trunion shaft 54 is placed on the end of the shaft by magnetic pad or adhesive pad 46 as shown in FIG. 3b. The vibration sensor 18 for the worm shaft 48 is as is shown in FIG. 3c placed on the outer ring of the worm shaft bearing assembly. Again a magnetic or adhesive pad 50 can be used.

Figure 4:
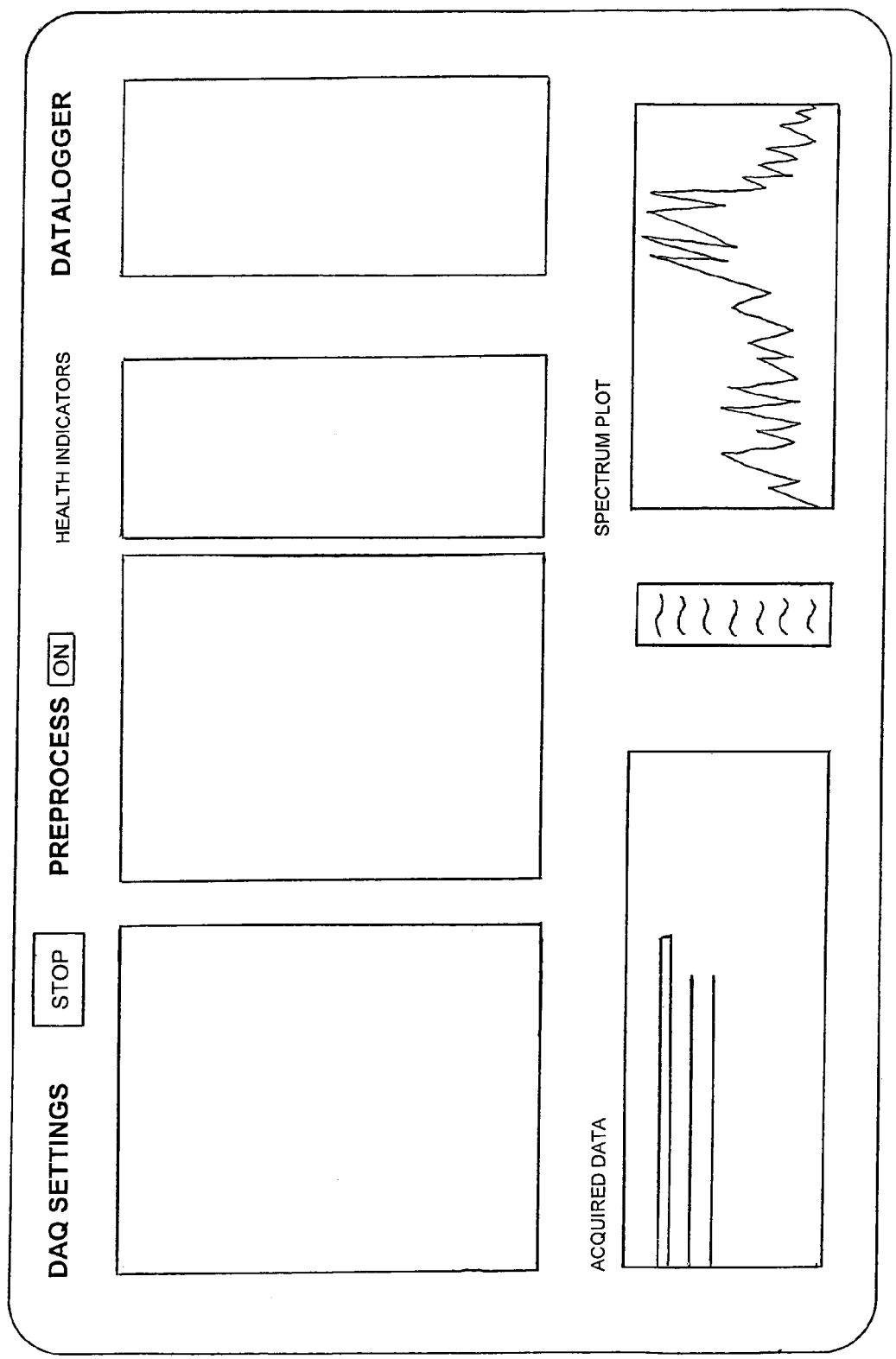
FIG. 4 shows the user interface for the stand alone PC that was in one embodiment part of the data acquisition system.

A software system was implemented in stand alone PC 32 to record and analyze the data. FIG. 4 shows the user interface for the stand alone PC. The software system performs the following functions:

collects signals from all channels and stores them on a tape recorder;

converts the data into corresponding engineering units and performs a FFT analysis;

uses power spectrum analysis of the journal spring shaft displacement to identify the main shaft and roller rotation frequencies and further estimate the roller wear;

uses the well known vibration pattern signature and/or order analysis method to detect gearbox, roller bearing wear and other major rotation parts' failure;

calculates the mill health indicator based on vibration and operation parameters; and reports/displays the result.

To calculate the roller diameters through frequency analysis, the following equations are used:

$$D = \frac{F_b}{F_r} D_b$$

Here,

D—roller diameter $F_r$—roller frequency from power spectrum analysis $F_b$—bowl frequency (main frequency of the system) from power spectrum analysis $D_b$—Bowl diameter, it is constant for a particular mill Cup type wear mode is commonly found in the roller wear process. When a wear cup occurs on the roller, double (sometimes multiple) roller frequencies appear in the power spectrum frequency analysis. In this case, the depth of the wear cup is estimated by using the following equations under the assumption that two or more equivalent roller diameters will take effect in the roller frequency generation around the major one:

$$D_1 = 2R_1 = \frac{F_b}{F_{r1}} D_b$$

$$D_2 = 2R_2 = \frac{F_b}{F_{r2}} D_b$$

$$H = R_1 - R_2 = \frac{|F_{r2} - F_{r1}| F_b D_b}{2 F_{r1} F_{r2}}$$

where, $F_{r1}$—dominant roller frequency peak from power spectrum analysis $F_{r2}$—secondary roller frequency peak from power spectrum analysis H—the depth of wear cup.

Figure 5A:
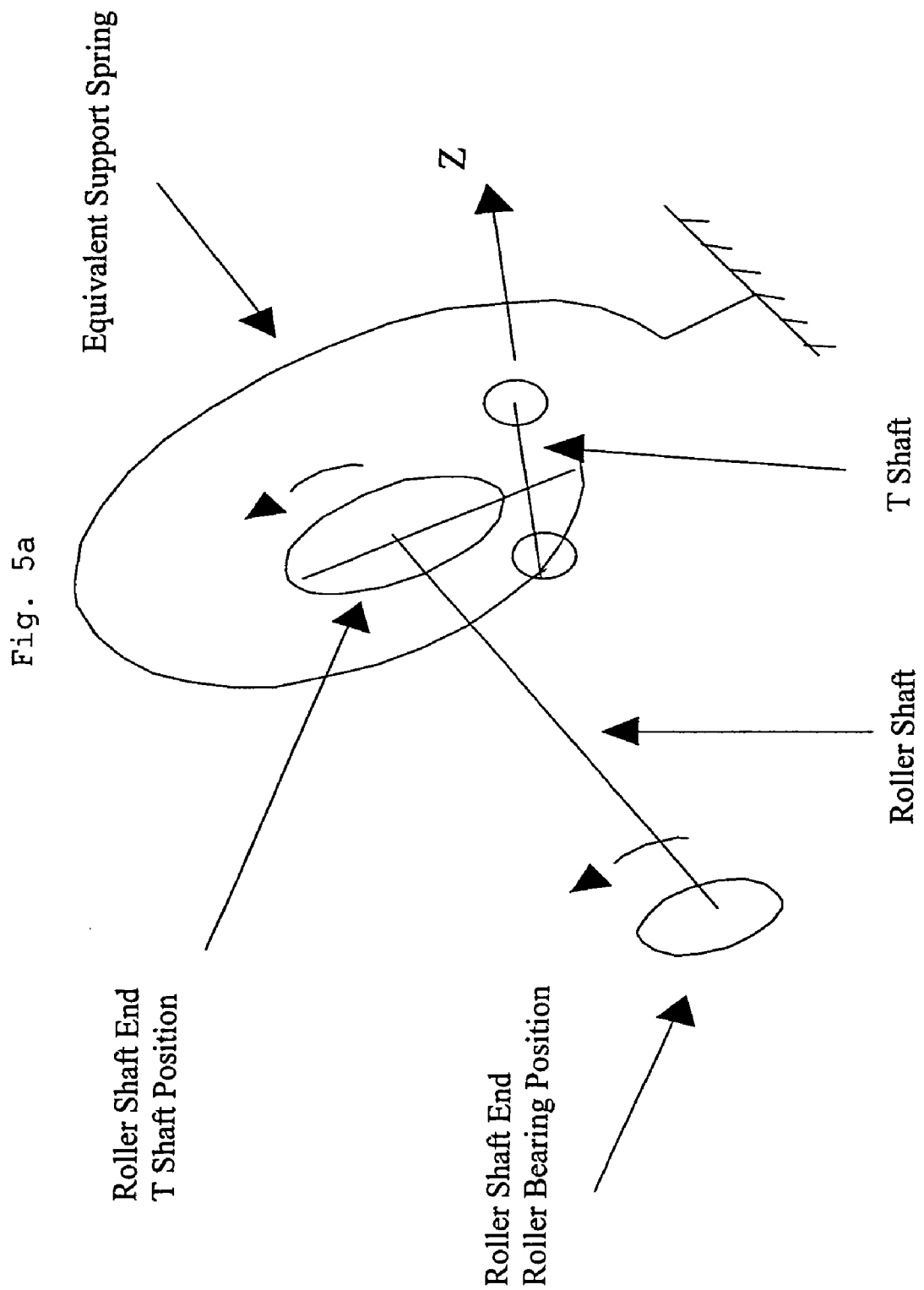
FIG. 5a shows a model for the roller trunion system of the Roll-Bowl mill and FIG. 5b shows the mill of FIG. 1 with the trunion, journal spring and roller shafts easily identifiable.
Figure 5B:
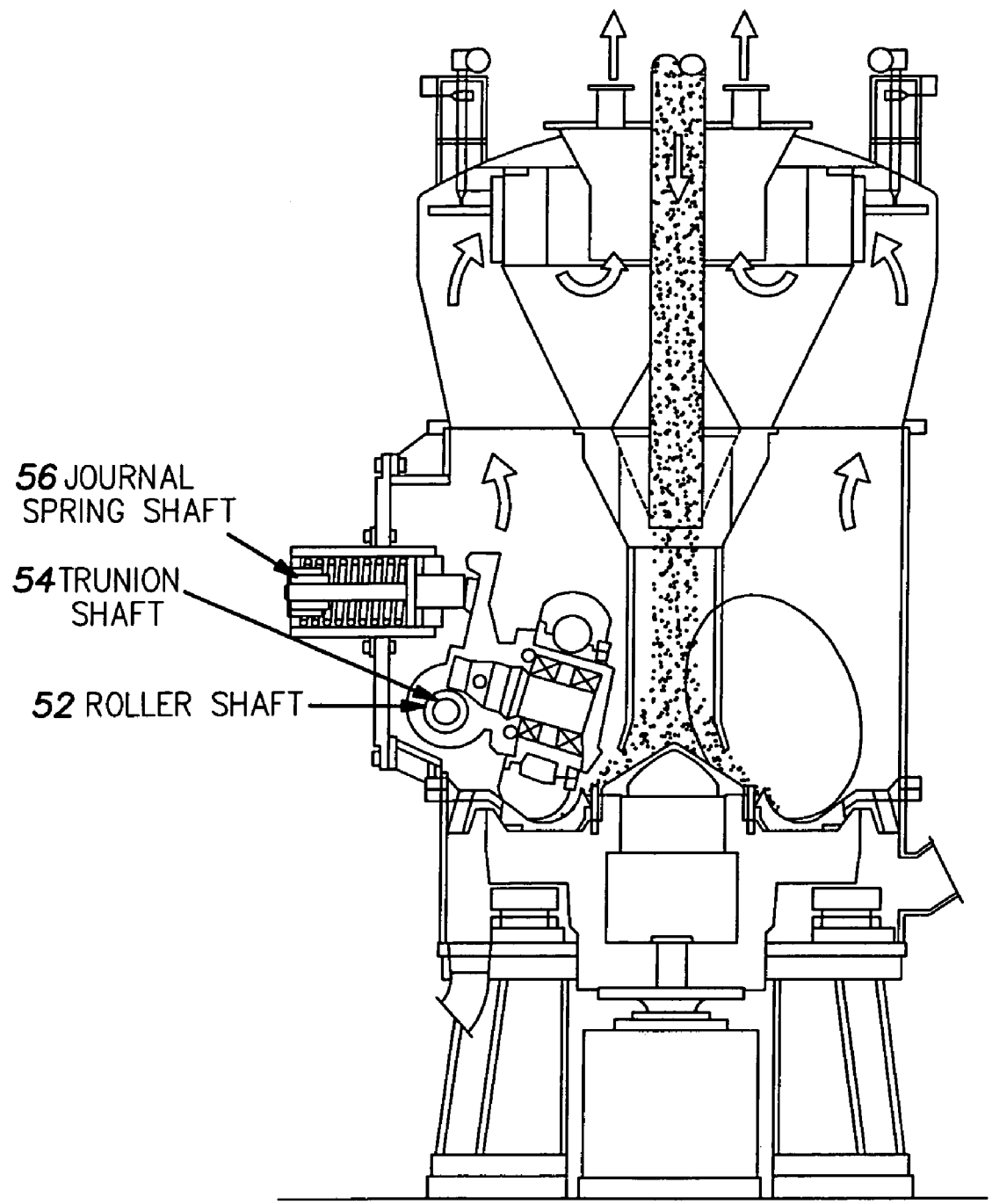

A roller-trunion system for mill 10 was modeled in vibration aspect. The vibration signal transfer function is built to be used in moving part failure prediction through vibration monitoring. The model for the roller-trunion system is illustrated in FIG. 5a. The model shows the T, that is, trunion, shaft, the roller shaft including the end of the roller shaft adjacent the roller bearing and the end of the roller shaft adjacent the position of the T shaft and the equivalent support spring for the shafts. The roller shaft is rigidly connected to the trunion shaft and as is shown in FIG. 5b, which is another drawing of the mill 10 shown in FIG. 1, the roller shaft 52, trunion shaft 54 and journal spring shaft 56 are components of the assembly that holds each of the rollers and applies a preload for each of the rollers.

The movement equations of torsional vibration of roller shaft ends due to excitation force from roller bearing can be expressed as $$J\ddot{\phi} + c\dot{\phi} + K_{Shaft}(\phi - \phi') = fr \quad (1)$$

$$J'\ddot{\phi}' + c'\dot{\phi}' + K_{Shaft}(\phi' - \phi) + K_{Support}\phi' = 0 \quad (2)$$

And the displacement of T (trunion) shaft end can be determined by $$z' = \phi'L \quad (3)$$

Let $$f = Fe^{i\omega t}, \phi = Ae^{i\omega t}, \phi' = A'e^{i\omega t}, z' = Z'e^{i\omega t} \quad (4)$$

Substituting into Equation (1), (2) and (3) leads to $$\begin{bmatrix} K_{Shaft} - \omega^2 J + i\omega c & -K_{Shaft} \\ -K_{Shaft} & K_{Shaft} + K_{Support} - \omega^2 J' + i\omega c' \end{bmatrix} \begin{pmatrix} A \\ A' \end{pmatrix} = \begin{pmatrix} Fr \\ 0 \end{pmatrix} \quad (5)$$

$$Z' = LA' \quad (6)$$

The transfer function can be obtained as $$\frac{A}{F} = \frac{r(K_{Shaft} + K_{Support} - \omega^2 J' + i\omega c')}{(K_{Shaft} - \omega^2 J + i\omega c)(K_{Shaft} + K_{Support} - \omega^2 J' + i\omega c') - K_{Shaft}^2} \quad (7)$$

$$\frac{A'}{F} = \frac{rK_{Shaft}}{(K_{Shaft} - \omega^2 J + i\omega c)(K_{Shaft} + K_{Support} - \omega^2 J' + i\omega c') - K_{Shaft}^2} \quad (8)$$

$$\frac{Z'}{F} = L\frac{A'}{F} \quad (9)$$

$$= \frac{rLK_{Shaft}}{(K_{Shaft} - \omega^2 J + i\omega c)(K_{Shaft} + K_{Support} - \omega^2 J' + i\omega c') - K_{Shaft}^2}$$

Figure 6:
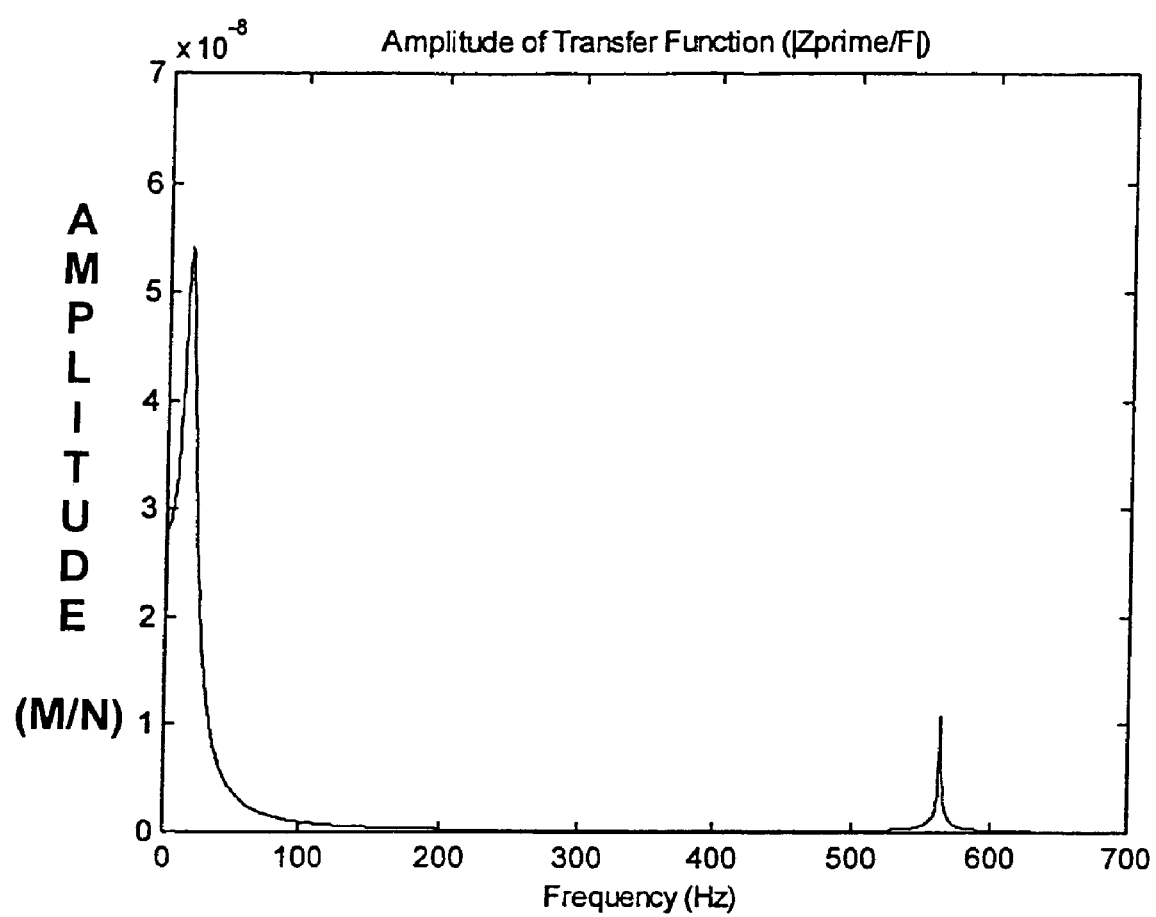
FIG. 6 shows using data from an typical mill a plot for the transfer function that is used to determine the amplitude of the tangential force of the roller bearing of the mill.

The amplitude of the tangential force of the bearing can be calculated as:

$$|F| = \frac{|Z'|}{\left|\frac{Z'}{F}\right|} = \frac{|A|}{\omega^2 \left|\frac{Z'}{F}\right|} \quad (10)$$

where |A| is the amplitude of acceleration measured at T shaft end in the Z direction. Using a data set from a typical mill, the transfer function to be simulated and plotted is shown in FIG. 6.

A health indicator is calculated to represent the health condition of the coal mill. The health indicator formula is based on the following assumptions:

The failure of each component of mill 10 has its own contribution to the overall failure of the mill. As can be appreciated the failure contribution of each component is or may be different than the failure contribution of the other components to the overall mill failure.

Mill availability, in terms of variation from normal operating condition and process parameters, are identifiable for major components of the mill 10.

Based on a general probability rule, the calculation formula is as follows:

$$P = \sum_{1}^{n} w_i p_i$$

where, P is the health indicator (availability of the mill), $0 \leq P \leq 1$; $w_i$ is the weight factor, $\Sigma w_i = 1$; $p_i$ is the availability of each individual component of the mill, $0 \leq p_i \leq 1$.

The components can be but are not limited to the following parameters:

1) Journal displacement from LVDT
2) Pressure difference across the bowl
3) Roller wear condition
4) Roller bearing condition
5) Mill body vibration
6) Mill worm shaft vibration
7) Outlet temperature
8) Driving motor input AMPs and coal feed rate.

The following is a typical set of formulas with a brief description for each of the above parameters:

1) Journal displacement measurement shows the thickness of coal in the pulverizer 10. Too little or too much coal in the mill 10 indicates a mill health problem.

$$P_1 = 1 - \alpha_1 \frac{|L| - |L_0|}{|L_0|}, w_1 = 0.1$$

Here, L is the measured LVDT value; L0 is nominal LVDT value; $w_1$ is the weight factor and $\alpha_1$ is a coefficient.

2) Pressure difference across the bowl should keep a certain value for normal operation condition.

$$P_2 = 1 - \alpha_2 \frac{|P| - |P_0|}{|P_0|}, w_2 = 0.08$$

Here, P is measured pressure difference value; P0 is nominal value.

3) Roller wear condition is determined by analyzing the main shaft and roller frequencies. The closer the roller frequency is to the main shaft frequency, the worse is the wear condition.

$$P_3 = 1 - \alpha_3 \frac{F_r - F_m}{F_m}, w_3 = 0.12$$

Here, Fr is roller frequency; Fm is main shaft frequency.

4) Roller bearing condition is detected by the vibration monitoring system through the vibration sensor on the end of trunion shaft for each roller. Using the bearing tune frequency and bench mark methods, the condition of the roller bearing condition is estimated.

$P_4 = 1 - SOBF, w_4 = 0.15$

Here, SOBF is a numerical value for Severity Of Bearing Failure. $0 < SOBF < 1$.

5) Mill body vibration tells the overall vibration condition of the mill. The health indicator is reduced when the amplitude of the vibration exceeds the nominal bench mark value.

$$P_5 = \begin{cases} 1 - \alpha_5 \dfrac{A - A_0}{A_0}, A < A_0 \\ 1, A \leq A_0 \end{cases}, w_5 = 0.15$$

Here, A is amplitude of measured body vibration; A0 is the nominal or benchmark value of the vibration.

6) Worm shaft vibration is considered in the similar way as body vibration.

$$P_6 = \begin{cases} 1 - \alpha_6 \dfrac{A - A_0}{A_0}, A < A_0 \\ 1, A \leq A_0 \end{cases}, w_6 = 0.15$$

Here, A is amplitude of measured worm shaft vibration and A0 is the nominal value of A.

7) Outlet temperature should not be away from its set value. Deviation from the set value will affect the mill health condition.

$$P_7 = 1 - \alpha_7 \frac{T - T_0}{T_0}, w_7 = 0.1$$

Here, T is the measured outlet temperature and T0 is its set value.

8) The ratio of driving motor input AMPs and coal feed rate represents the pulverizing efficiency of a mill. Decreasing of this ratio indicates the decline of the mill health condition.

$$P_8 = 1 - \alpha_8 \frac{R - R_0}{R_0}, w_8 = 0.15$$

Figure 7:
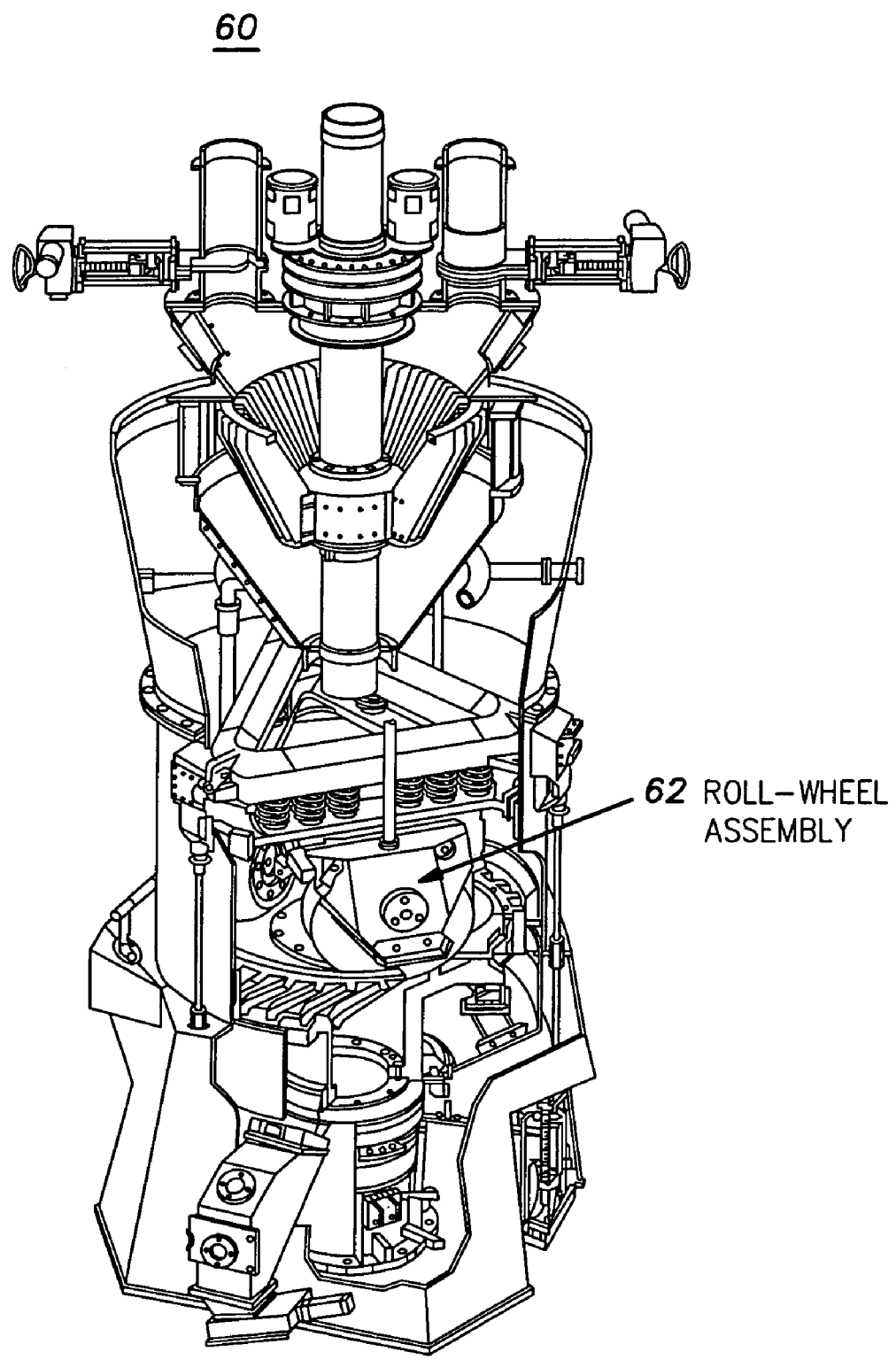
FIG. 7 shows another embodiment for a roll-bowl type pulverizing mill.

While the present invention is described herein with respect to an embodiment for a CE RS type roll bowl mill it should be appreciated that the invention may also be used with other types of roll bowl mills such as the Roll Wheel™ (previously known as the MSP) type roll bowl mill sold as of the filing date of the U.S. patent application by The Babcock and Wilcox Company shown in FIG. 7 as 60. Mill 60 includes three roll wheel assemblies 62.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. In combination:
a roll-bowl type mill for pulverizing solid fuels for use in firing a steam generator, said pulverizing mill comprising:
a) a bowl having a predetermined diameter;
b) one or more rollers each connected to an assembly through an associated roller bearing, said assembly for holding each of said one or more rollers and for applying a preload on each of said one or more rollers, each of said one or more rollers located a predetermined distance above said bowl; and
c) one or more linear transducers mounted on said assembly to measure displacement of said assembly when said mill is operating; and
a data acquisition system having as an input said displacement of said assembly measured by said one or more linear transducers, said data acquisition system comprising:
a computing device, operable to perform data collection and frequency power spectrum analysis of said displacement of said assembly to determine:
a) the diameter, D, of each of said one or more rollers by using a formula:

$$D = \frac{F_b}{F_r} D_b$$

b) where, $F_b$ is a frequency of said bowl and $F_r$ is a frequency of determined by power spectrum analysis respectively, and $D_b$ is said predetermined diameter of said bowl.

2. The combination of claim 1 wherein said computing device further determines a reduction and/or depth of wear cup, H, of each of said one or more rollers by using a formula:

$$D_1 = 2R_1 = \frac{F_b}{F_{r1}} D_b$$

$$D_2 = 2R_2 = \frac{F_b}{F_{r2}} D_b$$

$$H = R_1 - R_2 = \frac{|F_{r2} - F_{r1}| F_b D_b}{2 F_{r1} F_{r2}}$$

where, $F_{r1}$ is a dominant roller frequency peak from power spectrum analysis $F_{r2}$ is a secondary roller frequency peak from power spectrum analysis.

3. The combination of claim 2 wherein said assembly comprises a journal spring shaft and wherein said computing device further determines a relative thickness of said solid fuel in said mill by using a formula:

$$L_1 = \beta \frac{|L| - |L_0|}{|L_0|},$$

where L is the value of a displacement of said journal spring shaft measured by said one or more linear transducers, $L_0$ is a calibrated value from said one or more transducers, and $\beta$ is a coefficient.

4. The combination of claim 1 wherein said mill further comprises a wall and a means having one or more vibration sensors mounted thereon for connecting said assembly onto said mill wall and said computing device determines wear of each of said one or more roller bearings by analyzing using vibration pattern signature and/or order analysis methods the signal from each of said one or more vibration sensors.

5. The combination of claim 4 wherein said connecting means comprises a trunion shaft.

6. The combination of claim 4 wherein said connecting means comprises said assembly.

7. In combination:
a roll-bowl type mill for, pulverizing solid fuels for use in firing a steam generator, said pulverizing mill comprising:
a) a bowl having a predetermined diameter;
b) one or more rollers each connected to an assembly through an associated roller bearing, said assembly for holding each of said one or more rollers and for applying a preload on each of said one or more rollers, said one or more rollers located a predetermined distance above said bowl; and
c) one or more linear transducers mounted on said assembly to measure displacement of said assembly when said mill is operating; and
a data acquisition system having as an input said displacement of said assembly measured by said one or more linear transducers, said data acquisition system comprising:
a computing device operable to perform, data collection and frequency power spectrum analysis of said displacement of said assembly to determine a reduction and/or depth of wear cup, H, of each of said one or more rollers by using a formula:

$$D_1 = 2R_1 = \frac{F_b}{F_{r1}} D_b$$

$$D_2 = 2R_2 = \frac{F_b}{F_{r2}} D_b$$

$$H = R_1 - R_2 = \frac{|F_{r2} - F_{r1}| F_b D_b}{2 F_{r1} F_{r2}}$$

where, $F_{r1}$ is a dominant roller frequency peak from power spectrum analysis $F_{r2}$ is a secondary roller frequency peak from power spectrum analysis.

8. In combination:
a roll-bowl type mill for pulverizing solid fuels for use in firing a steam generator, said pulverizing mill comprising:
a) a bowl having a predetermined diameter;
b) one or more rollers each connected to an assembly through an associated roller bearing, said assembly comprising a journal spring shaft and being operable to hold each of said one or more rollers and to apply a preload on each of said one or more rollers, said one or more rollers located a predetermined distance above said bowl; and
c) one or more linear transducers mounted on said assembly to measure a displacement of said assembly when said mill is operating; and
a data acquisition system having as an input said displacement of said assembly measured by said one or more linear transducers, said data acquisition system comprising:
a computing device operable to perform data collection and frequency power spectrum analysis of said displacement of said assembly to determine a relative thickness $L_1$ of said solid fuel in said mill by using a formula:

$$L_1 = \beta \frac{|L| - |L_0|}{|L_0|},$$

where L is the value of a displacement of said journal spring shaft measured by said one or more linear transducers, $L_0$ is a calibrated value from said one or more transducers, and $\beta$ is a coefficient.

9. The combination of claim 8, wherein the mill has a predetermined number of operational components, and wherein the computing device is operable to determine an indicator P, where 0<P<1, for presenting availability of said mill to perform said solid fuel pulverizing by using a formula:

$$P = \sum_1^n w_i p_i$$

where $w_i$ is a weight factor, $\Sigma w_i = 1$; and $p_i$ is availability of each individual operational component of said predetermined number of components and $0 \leq p_i \leq 1$.

10. The combination of claim 9, wherein the availabilities of the predetermined operational components comprises $P_1$, which relates to the thickness of the solid fuel and is equal to $1-L_1$.

11. The combination of claim 10, wherein the availabilities of the predetermined operational components further comprises:
$P_2$, which relates to a pressure difference across the bowl and is determined from a formula:

$$P_2 = 1 - \alpha_2 \frac{|P| - |P_0|}{|P_0|}$$

where P is a measured pressure difference across the bowl, $P_0$ is a nominal pressure difference value and $\alpha_2$ is a coefficient.

* * * * *